United States Patent [19]

Shimomura et al.

[11] Patent Number: 5,538,731
[45] Date of Patent: Jul. 23, 1996

[54] COSMETIC

[75] Inventors: Kenji Shimomura, Ise; Masami Nakamura, Toba, both of Japan

[73] Assignee: Mikimoto Pharmaceutical Co., Ltd., Mie-ken, Japan

[21] Appl. No.: 342,785

[22] Filed: Nov. 21, 1994

Related U.S. Application Data

[63] Continuation of Ser. No. 47,788, Apr. 15, 1993, abandoned.

[30] Foreign Application Priority Data

Apr. 24, 1992 [JP] Japan ................................ 4-129822

[51] Int. Cl.⁶ ............................. A61K 7/00; A61K 7/48
[52] U.S. Cl. ........................ 424/401; 424/62; 424/195.1
[58] Field of Search ......................... 424/401, 62, 195.1; 514/844

[56] References Cited

FOREIGN PATENT DOCUMENTS

| | | |
|---|---|---|
| 54-59311 | 10/1977 | Japan . |
| 60-64983 | 7/1981 | Japan . |
| 60-64996 | 7/1981 | Japan . |
| 61-85324 | 4/1986 | Japan . |
| 3044316 | 2/1991 | Japan . |
| 3-258711 | 11/1991 | Japan . |
| 5-306214 | 11/1993 | Japan . |
| 7188045 | 7/1995 | Japan . |

OTHER PUBLICATIONS

Huxley et al., The New Royal Horticultural Society Dictionary Of Gardening, vol. 4, p. 496, (1992).

*Primary Examiner*—Melvyn I. Marquis
*Attorney, Agent, or Firm*—Darby & Darby

[57] ABSTRACT

A cosmetic containing a solvent extract of trapae fructus according to the present invention has a large skin depigmental action, and inhibits a hyaluronidase action. In consequence, the lubricity and flexibility of the skin are maintained and aging is also prevented. In addition, the cosmetic of the present invention inhibits the production of active oxygen and has antioxydation, and therefore the oxidation of fatty acids is prevented, so that the production of peroxides is suppressed, which leads to the prevention of the aging of the skin. Therefore, the cosmetic of the present invention prevents rough skin and keep skin luster and skin elasticity in a good state. The safety of the trapae fructus to the skin of humans has been assured by using it as food for a long period of time.

8 Claims, No Drawings

COSMETIC

This is a continuation-in-part, of application Ser. No. 08/047,788 filed Apr. 15, 1993, now abandoned.

BACKGROUND OF THE INVENTION

1. Field of the Invention

The present invention relates to a cosmetic which has a high skin depigmental action, inhibits the action of hyaluronidase, and is effective for the prevention of rough skin.

2. Description of the Prior Art

Trapae fructus belongs to a dicotyledoneae, archichlamydeae and myrtiflorae order hydrocatyaceae family and is called Trapa natans L. in accordance with botanical nomenclature, and this trapae fructus is what is obtained by drying fruits of a plant usually called hydrocatyaceae.

The hydrocatyaceae is distributed in the Temperate Zones and the subtropical zones of Japan, Taiwan, Korea and China, and it is an annual and eatable plant which grows in ponds and swamps.

The hydrocatyaceae can be used as a nourishing food and tonic or a medicine for fever.

Various substances having a skin depigmental action have been used and known as raw materials of cosmetics, and applications of synthetic substances having such an action are limited, because their safety is not insured in the case that they are applied to the skins of humans for a long period of time. On the other hand, most of natural substances are poor in the skin depigmental action.

Nowadays, a natural substance is desired in which safety to the skin of humans has been assured by using it as men's food for a long period of time and which has the strong skin depigmenstal action and other effects to the skin.

SUMMARY OF THE INVENTION

An object of the present invention is to provide a cosmetic which is safe to the skin of humans, has a high skin depigmental action, inhibits the action of hyaluronidase, and contains components effective for rough skin.

Features of the present invention are as follows:

(1) A cosmetic comprising a solvent extract of trapae fructus.

(2) The cosmetic described in the preceding paragraph (1) wherein the solvent extract is what is extracted with water and/or a hydrophilic organic solvent.

(3) The cosmetic described in the preceding paragraph (2) wherein the hydrophilic organic solvent is at least one selected from the group consisting of ethanol, glycerin, 1,3-butylene glycol and propylene glycol.

(4) The cosmetic described in the preceding paragraph (2) wherein the extraction solvent is water and/or ethanol.

(5) The cosmetic described in the preceding paragraph (1) wherein the solvent extract is a powder obtained by lyophilizing a liquid extract.

(6) The cosmetic described in any one of the preceding paragraphs (1) to (5) wherein the conformation of the cosmetic is one selected from the group consisting of lotion, cream, milky lotion and pack.

DETAILED DESCRIPTION OF THE INVENTION

In order to solve the above-mentioned problems, the present inventors have screened plants in which their safety to humans has been confirmed by using them as foods for a long period of time, and then investigated some of these plants which are worth utilizing as cosmetics.

As a result, they have found that trapae fructus is very effective as a raw material for cosmetics or as a quasi-drug.

It has been confirmed that the trapae fructus has a skin depigmenstal action, the activity inhibition of hyaluronidase, active oxygen inhibition and antioxydation properties.

For the utilization of the trapae fructus, extraction is carried out with water or a hydrophilic organic solvent such as ethanol, methanol or acetone. However, since this extraction is done in order to obtain the raw material of a cosmetic, it is naturally preferable to achieve the extraction with water, ethanol or a mixed solvent thereof.

In a certain case, a polyhydric alcohol such as glycerin, 1,3-butylene glycol or propylene glycol, or a mixed solution of the polyhydric alcohol and water can be utilized in the extraction.

In addition, the resultant extract may be lyophilized to form a powder, and thus it is also effective to utilize the trapae fructus in the form of the powder.

The extracted substance can be mixed with a liquid oil such as squalane or jojoba oil, a solid oil such as beewax or cetyl alcohol, an activator, a wetness keeping agent such as glycerin or 1,3-butylene glycol, and a medicinal substance to prepare a cosmetic in a desired conformation. For example, the conformation of the cosmetic can be selected from the group consisting of lotion, cream, milky lotion, pack and the like in compliance with an intended purpose.

The first effect of the extract regarding the present invention is the skin depigmenstal action, as described above. The second effect of the extract is the activity inhibition of hyaluronidase. This hyaluronidase is an enzyme which is widely distributed in an organism and is present even in the skin, and it can decompose hyaluronic acid according to its literal sense. Hyaluronic acid is a straight-chain polysaccharide in which β-D-N-acetylglucosamine and β-D-glucuronic acid are alternately bonded, and it is a kind of glucosaminoglucan which is widely distributed in connection tissues of a mammal together with chondroitin sulfuric acid and the like.

It is considered that in the connective tissue, hyaluronic acid functions to hold water in spaces among cells, to form jelly matrixes for the purpose of holding the cells, to keep lubricity and flexibility of the skin, to withstand external force (mechanical damage) and to prevent bacterial infection. It is also considered that the amount of hyaluronic acid in the skin decreases with aging, which leads to aging phenomenons such as slight furrows and dryness of the skin.

Therefore, the activity inhibition of hyaluronidase which decomposes this hyaluronic acid can be presumed to contribute to the stability of hyaluronic acid used in a drug, hyaluronic acid in the drug applied on the skin, and hyaluronic acid having been presented in the skin.

The third effect of the extract regarding the present invention is the action of active oxygen inhibition. Oxygen is present in the air, and organisms (except anaerobes) cannot live without oxygen. However, oxygen can become active oxygen under the influence of ultraviolet rays, an enzyme and the like. This active oxygen oxidizes fatty acids to produce peroxides. Furthermore, it also oxidizes phospholipids in organic membranes of the organism to damage them.

In addition, it is considered that the thus produced peroxides and active oxygen damage DNA and accelerate the aging. This active oxygen affects a mechanism for producing melanin from tyrosine to bring about the melanism of the skin. Thus, the inhibition of the active oxygen is important for the skin and in other words, it is an important factor required for the cosmetic.

The trapae fructus of the present invention also has the functions of this active oxygen inhibition and antioxydation properties.

EXAMPLES

Now, the present invention will be described in detail in reference to examples which are embodiments of actual utilization, but the scope of the present invention should not be limited to these examples.

Preparation examples of trapae fructus extracts used in the present invention are as follows.

Preparation Example 1

300 ml of ethanol were added to 10 g of trapae fructus (a dried product), and the resultant mixture was then allowed to stand for 5 days with stirring sometimes. Afterward, the mixture was filtered and then lyophilized.

Preparation Example 2

300 ml of a 50% aqueous ethanol solution were added to 10 g of trapae fructus (a dried product), and the resultant mixture was then allowed to stand for 5 days with stirring sometimes. Afterward, the mixture was filtered and then lyophilized.

Preparation Example 3

300 ml of purified water were added to 10 g of trapae fructus (a dried product), and the resultant mixture was then heated for 3 hours. Afterward, the mixture was allowed to cool, filtered, and then lyophilized.

| Example 1 (Lotion) | (wt %) |
| --- | --- |
| Olive oil | 0.5 |
| Ethanol extract of *trapae fructus* in Preparation Example 1 | 0.5 |
| Polyoxyethylene (20 E.O.) sorbitan monostearate | 2.0 |
| Polyoxyethylene (60 E.O.) hardened caster oil | 2.0 |
| Ethanol | 10.0 |
| 1.0% aqueous sodium hyaluronate solution | 5.0 |
| Purified water | 80.0 |

| Example 2 (Cream) | | (wt %) |
| --- | --- | --- |
| A | Squalane | 20.0 |
| | Olive oil | 2.0 |
| | Mink oil | 1.0 |
| | Jojoba oil | 5.0 |
| | Beewax | 5.0 |
| | Setostearyl alcohol | 2.0 |
| | Glycerin monostearate | 1.0 |
| | Sorbitan monostearate | 2.0 |
| | 50% ethanol extract of *trapae fructus* in Preparation Example 2 | 1.0 |
| B | Purified water | 47.9 |
| | Polyoxyethylene (20 E.O.) sorbitan monostearate | 2.0 |
| | Polyoxyethylene (60 E.O.) hardened caster oil | 1.0 |
| | Glycerine | 5.0 |
| | 1.0% aqueous sodium hyaluronate solution | 5.0 |
| | Methyl paraoxybenzoate | 0.1 |

The materials A and B were separately weighed, and they were then heated to 70° C. The material A was slowly added to the material B, and the mixture was then slowly cooled to 30° C. with stirring.

Example 3

Example 3 is connected with a cream prepared by the same procedure as in Example 2 except that an extract of Preparation Example 2 was replaced with that of Preparation Example 3.

(Inhibition of tyrosinase activity)
(Test procedure)

In a screw vial were placed 0.9 ml of a McIlvalne buffer solution, 1.0 ml of a 1.66 mM Tyrosine solution and 1.0 ml of a 0.1 wt./vol.% aqueous solution of a lyophilized product in the above-mentioned preparation example (If it was difficult to dissolve the lyophilized product, and thus ethanol was added, whereby it was dissolved, and purified water was further added thereto. Next, evaporation was carried out to remove ethanol, and the concentration of the lyophilized product was then adjusted so as to be 0.1 wt./vol.%.), and the solution was then warmed for 5 minutes or more in a thermostatic bath at 37° C.

Afterward, 0.1 ml of a tyrosinase solution (made by Sigma Co., Ltd.; derived from mushroom; 914 units/ml) was added to the solution, and it was then kept up in the thermostatic bath at 37° C. After 10 minutes, absorbance was measured at 475 nm.

A control was prepared by a similar procedure except that the above-mentioned sample solution was replaced with pure water, and the absorbance was then measured in the same manner.

In this test, the end concentration of the sample was 0.033%.

(Calculation formula)

Tyrosinase activity inhibition ratio (%)=

$$\{B-(A-P)\}/B \times 100$$

wherein

A: absorbance of the sample,

B: absorbance of the control, and

P: absorbance attributed to coloring of the sample (diluted thrice).

TABLE 1

| Specimen | Tyrosinase Activity Inhibition Ratio |
| --- | --- |
| Preparation Example 1 | 84.0 |
| Preparation Example 2 | 72.0 |
| Preparation Example 3 | 35.2 |

(Test of hyaluronidase activity inhibition)
(Test procedure)

6 g of a 0.1M (pH=6.0) phosphoric acid buffer solution containing 0.4% of sodium hyaluronate were weighed, and it was then allowed to stand in a thermostatic bath at 37° C. for 5 minutes. Afterward, 1.0 ml of a 0.1 wt./vol.% aqueous solution of a lyophilized product in the above-mentioned preparation example was added (If it was difficult to dissolve the lyophilized product, and thus ethanol was added, whereby it was dissolved, and purified water was further added thereto. Next, evaporation was carried out to remove ethanol, and the concentration of the lyophilized product was then adjusted so as to be 0.1 wt./vol.%.), followed by stirring. Afterward, 1 ml of a 0.1M (pH=6.0) phosphoric acid buffer solution containing 0.01% of hyaluronidase (type I-S, derived from bull testicles, made by Sigma Co., Ltd.) was added thereto, and the solution was immediately stirred. 6 ml of the solution were placed in an Ostwald viscometer in a thermostatic bath at 37° C. The viscosity of the solution was measured after 1 minute, 5 minutes, 10 minutes, 20 minutes and 40 minutes.

A control was prepared by a similar procedure except that the above-mentioned sample solution was replaced with pure water, and the viscosity was then measured in the same manner.

In this test, the end concentration of the sample was 0.0125%.

The viscosity of the solution after 1 minute was regarded as 100, and the results are represented by indexes in Tables 2 and 3.

TABLE 2

| Specimen | After 5 min. | After 10 min. | After 20 min. | After 40 min. |
|---|---|---|---|---|
| Control | 63.3 | 44.0 | 28.2 | 18.5 |
| Preparation Example 1 | 100.0 | 99.5 | 99.4 | 99.3 |

TABLE 3

| Specimen | After 5 min. | After 10 min. | After 20 min. | After 40 min. |
|---|---|---|---|---|
| Control | 65.2 | 55.0 | 28.3 | 18.2 |
| Preparation Example 1 | 99.4 | 99.5 | 99.3 | 99.3 |
| Preparation Example 2 | 99.3 | 99.4 | 99.4 | 99.1 |

(Test of active oxygen inhibition effect)

The inhibition effect of active oxygen can be measured by various methods, but in this test, the following procedure was utilized.

| | |
|---|---|
| 50 mM potassium phosphate buffer solution (pH = 7.8) (containing 1.3 mM DETAPAC) | 133 ml |
| The above potassium phosphate buffer solution of 40 units/ml catalase | 5 ml |
| The above potassium phosphate buffer solution of 2 mM nitrobluetetrazolium | 5 ml |
| The above potassium phosphate buffer solution of 1.8 mM xanthine | 17 ml |
| | 160 ml |

0.3 ml of a specimens was added to 2.4 ml of the above-mentioned mixture which was a reagent, and 0.3 ml of a xanthine oxidase solution (which was previously regulated with the above-mentioned potassium phosphate buffer solution so that absorbance might rise about 0.02 per minute, when an experiment was made using water as a specimens) was further added. Immediately, the absorbance (560 nm) was measured (the measurement was carried out for 2 minutes, and the linearity of the absorbance was confirmed).

Calculation formula

Inhibition ratio=[(A-B)/A]×100 wherein

A: change of the absorbance per minute when the specimens was water, and

B: change of the absorbance of the specimens per minute.

With regard to concentration, some experiments were made to find a concentration at which the active oxygen production inhibition ratio was 50%. The specimens was an aqueous solution of a lyophilized product of the above-mentioned preparation example having a suitable concentration (If it was difficult to dissolve the lyophilized product, and thus ethanol was added, whereby it was dissolved, and purified water was further added thereto. Next, evaporation was carried out to remove ethanol, and the concentration of the lyophilized product was then adjusted so as to be the suitable concentration).

TABLE 4

| Specimen | Conc. at Which Active Oxygen Production Inhibition Ratio was 50% (End Conc. %) |
|---|---|
| Preparation Example 1 | 0.00006 |
| Preparation Example 2 | 0.00003 |
| Preparation Example 3 | 0.00003 |

(Antioxydation test)

In a 50 ml test tube with a screw cap, the following test solution was prepared.

| | |
|---|---|
| Specimen | 5 mg |
| 2% linoleic acid solution in ethanol | 10 ml |
| 0.1 M phosphoric acid buffer solution (pH = 7.0) | 10 ml |
| Purified water | 5 ml |

This test solution was allowed to stand in a thermostatic bath at 50° C., while light was shut out.

The following measurements were done, prior to placing the test solution in the thermostatic bath (after 0 day), after 3 days, 6 days and 8 days.

12.125 ml of 75% ethanol and 0.125 ml of 30% ammonium thiocyanate were added to 0.125 ml of the test solution, and the solution was stirred and then allowed to stand for 3 minutes. Afterward, 0.125 ml of a 3.5% aqueous HCl solution including 0.02 N ferrous chloride was added thereto, and the solution was stirred and then allowed to stand for 3 minutes. Next, absorbance was measured at a wavelength of 500 nm. A cell length was 10 mm, and a control was prepared by replacing the test solution with water.

TABLE 5

| Specimen | After 0 day | After 3 days | After 5 days | After 7 days |
|---|---|---|---|---|
| Water | 0.014 | 0.050 | 0.103 | 0.262 |
| Preparation Example 1 | 0.018 | 0.035 | 0.054 | 0.055 |
| Preparation Example 2 | 0.014 | 0.026 | 0.033 | 0.035 |
| Preparation Example 3 | 0.016 | 0.028 | 0.041 | 0.040 |
| Vitamin E* | 0.015 | 0.026 | 0.047 | 0.070 |
| BHT** | 0.011 | 0.020 | 0.018 | 0.021 |

*Riken E Oil 700, made by Riken Vitamin Oil Co., Ltd.
**Dibutylhydroxytoluene (Use test)

Samples in examples and samples in comparative examples were used once or more per day on the left side and the right side of each face of 6 ladies, respectively, and after 3 months, a questionnaire regarding the sensuous difference between their left side cheeks and their right side cheeks was conducted. It should be noted that in the comparative examples (Comparative Examples 1 and 2), various extracts of trapae fructus prepared in the preparation examples and used in the examples were placed with water.

Furthermore, experiments were carried out by using the following samples in two groups of 12 ladies.

Sensuous Examination Program

| Experiment No. | Used Sample |
|---|---|
| 1 | Samples of Examples 1, 2 and Comp. Examples 1, 2 |
| 2 | Samples of Examples 1, 3 and Comp. Examples 1, 2 |

Evaluation was made on the basis of the following standard of sensuous examination marks. The examination marks of sensuous tests by 6 ladies are summed up and the sum total are set forth in Table 6.

3 . . . In the case that samples of the examples were very excellent.

2 . . . In the case that the samples of the examples were excellent.

1 . . . In the case that the samples of the examples were slightly excellent.

0 . . . In the case that no difference is between the samples of the examples and the comparative examples.

-1 . . . In the case of that the samples of the comparative examples were slightly excellent.

-2 ... In the case of that the samples of the comparative examples were excellent.

-3 . . . In the case of that the samples of the comparative examples were very excellent.

TABLE 6

| | Skin Depigmental Action | Rough Skin Prevention | Skin Luster | Skin Elasticity |
|---|---|---|---|---|
| Experiment No. 1 | 13 | 10 | 8 | 8 |
| Experiment No. 2 | 11 | 11 | 8 | 9 |

Thus, it will be seen that, with regard to each of the experiments, the skin depigmental action was excellent, while the rough skin prevention, skin luster, and skin elasticity were between slightly excellent and excellent, on average.

A cosmetic of the present invention is safe and suitable for skin, has a large skin depigmental action, and can inhibit a hyaluronidase action. In consequence, hyaluronic acid can be stabilized, so that the lubricity and flexibility of the skin can be maintained and aging can also be prevented. In addition, the cosmetic of the present invention has the functions of active oxygen inhibition and antioxidation, and therefore the oxidation of fatty acids can be prevented, so that the production of peroxides can be suppressed, which leads to the prevention of the aging and the melanism of the skin.

Therefore, the cosmetic of the present invention can prevent rough skin and keep skin luster and skin elasticity in a good state.

What is claimed is:

1. A cosmetic comprising a solvent extract of the whole fruit of trapae natans 1, fructus, wherein the extract is obtained by a single solvent extraction.

2. The cosmetic according to claim 1 wherein the extraction solvent is ethanol, containing up to 50 % water.

3. The cosmetic according to claim 1 wherein the solvent extract is a powder obtained by lyophilizing a liquid extract.

4. The cosmetic according to claim 1 wherein the conformation of the cosmetic is one selected from the group consisting of lotion, cream, milky lotion and pack.

5. The cosmetic according to claim 2 wherein the conformation of the cosmetic is one selected from the group consisting of lotion, cream, milky lotion and pack.

6. The cosmetic according to claim 3 wherein the conformation of the cosmetic is one selected from the group consisting of lotion, cream, milky lotion and pack.

7. The cosmetic according to claim 2 wherein said extraction solvent is in the range of 50% to 100% ethanol.

8. The cosmetic according to claim 7 wherein said extraction solvent is 50% ethanol.

* * * * *

UNITED STATES PATENT AND TRADEMARK OFFICE
CERTIFICATE OF CORRECTION

PATENT NO. : 5,538,731

DATED : July 23, 1996

INVENTOR(S) : Kenji SHIMOMURA and Masami NAKAMURA

It is certified that error appears in the above-indentified patent and that said Letters Patent is hereby corrected as shown below:

In the cover page of the patent, Section [30], please delete "4-129822" and insert therefor --HEI 4-129822--.

Signed and Sealed this

Twenty-second Day of October, 1996

Attest:

BRUCE LEHMAN

Attesting Officer     Commissioner of Patents and Trademarks